United States Patent

Rogozinski

[11] Patent Number: 5,888,226
[45] Date of Patent: Mar. 30, 1999

[54] INTERVERTEBRAL PROSTHETIC DISC

[76] Inventor: Chaim Rogozinski, 3716 University Blvd. South, Suite 3, Jacksonville, Fla. 32216

[21] Appl. No.: 968,412

[22] Filed: Nov. 12, 1997

[51] Int. Cl.[6] .................................................. A61F 2/44
[52] U.S. Cl. ................................................ 623/17
[58] Field of Search ................................ 623/17; 606/61

[56] References Cited

U.S. PATENT DOCUMENTS

| | | | |
|---|---|---|---|
| 4,714,469 | 12/1987 | Kenna | 623/17 |
| 4,863,477 | 9/1989 | Monson | 623/17 |
| 5,258,031 | 11/1993 | Salib | 623/17 |
| 5,306,307 | 4/1994 | Senter | 623/17 |
| 5,314,477 | 5/1994 | Marnay | 623/17 |
| 5,534,029 | 7/1996 | Shima | 623/17 |
| 5,556,431 | 9/1996 | Büttner-Janz | 623/17 |
| 5,645,596 | 7/1997 | Kim | 623/17 |
| 5,658,336 | 8/1997 | Pisharodi | 623/17 |
| 5,674,296 | 10/1997 | Bryan | 623/17 |

*Primary Examiner*—Michael J. Milano
*Attorney, Agent, or Firm*—Thomas C. Saitta

[57] ABSTRACT

A self-centering prosthetic disc to replace a disc in the spine, the disc having two opposing convex surfaces where the point of maximum vertical dimension is non-central. The disc may be utilized alone or in combination with one or two vertebral attachment members, the vertebral attachment members having concave surfaces corresponding to the convex surfaces of the disc.

58 Claims, 4 Drawing Sheets

INTERVERTEBRAL PROSTHETIC DISC

BACKGROUND OF THE INVENTION

The invention relates in general to a medical device structured to serve as a replacement for damaged, diseased, pathologic, degenerated or ruptured intervertebral discs, and more particularly to such a device which is self-centering and maintains the proper spatial relationship between adjacent vertebrae while allowing for movement of the adjacent vertebrae in a manner similar to and consistent with the range and type of motion found prior to pathology, degeneration or rupture.

In addressing the problems of pathologic, degenerated or ruptured intervertebral discs, the solutions have generally focused on immobilizing the adjacent vertebrae by fusion or replacement of the damaged disc with a prosthetic disc, where the prothesis is designed to allow for some motion between the adjacent vertebrae. A successful disc replacement requires a prosthetic device which remains properly positioned between the vertebrae, maintains the vertebrae in proper spaced relation, allows for a range of motion while maintaining proper alignment of the spine and vertebrae in the frontal and sagittal plane during such motion, is biocompatible and is of sufficient durability to withstand loading cycles of up to 100 million or more.

There have been numerous patents issued in this field. Some patents involve replacement discs composed of a compressible or elastic material, some involve discs comprising matrices to enhance bone growth into the discs, some involve discs composed of both rigid and non-rigid materials, and some involve rigid discs. Of the later type, some are designed to remain detached from the adjacent vertebrae while others are designed for direct connection to the vertebrae. Multi-component replacement discs are known where the plural components are free to move relative to each other. The major drawback from the known devices is that the range, angle and type of movement does not properly mimic the natural range, angle and type of motion found in the actual human disc, while maintaining proper frontal and sagittal alignment of the spine.

It is an object of the replacement intervertebral disc of the present invention to provide a device which substitutes for a human disc and successfully replicates the range, angle and type of movement between the adjacent vertebrae, where the disc is composed of a durable, rigid, biocompatible material of high fatigue strength so as to withstand millions of loading cycles without failure or degradation. It is a further object to provide such a disc having two generally convex surfaces which generally correspond to the disc being replaced and the concave shape of adjacent vertebrae, where the maximum dimension between the two convex surfaces is not central to the main body of the disc, where the disc is self-centering to preclude disc impingement into the spinal canal, and where proper intervertebral spacing is maintained by joining the two opposing convex surfaces by a generally vertically oriented wall member. It is a further object to provide such a disc where the convex surfaces are not in parallel relationship so as to better replicate the configuration of a human disc and proper spinal alignment.

SUMMARY OF THE INVENTION

In general the invention is an intervertebral disc prosthesis which is utilized as a replacement for damaged or diseased discs in the human spine. The disc acts as spacer which reconstitutes the original disc height to properly separate adjacent vertebrae. The disc is centered and stabilized within the spine by the combination of body weight, ligamentotaxis and the overall shape of the disc and the opposing surfaces of adjacent vertebrae. In its simplest form, the disc is a double convex main body, circular or elliptical at the periphery formed by the juncture of the two convex surfaces. The opposing convex surfaces have a non-central major vertical axis, defined as the vertical line at the point of greatest vertical dimension, which is distinct from the central vertical axis, defined as the vertical line at the midpoint of a disc with circular periphery and as the vertical line at the midpoint on the anterior-posterior axis of a disc with an elliptical or ovoid periphery. The anterior-posterior axis is defined as the horizontal line passing through the non-central major vertical axis and the central vertical axis. Thus a vertical cross-section taken along the anterior-posterior axis will have an ovoid shape. The disc is preferably bilaterally symmetric, but may be asymmetric if required to conform to a particular patient anatomy. This configuration best conforms to the natural shape of the endplate of a vertebra, thereby providing for optimum rotation and sliding moments and translations. The disc is surgically inserted between adjoining vertebrae, and the concave endplates retain the disc in position.

In a most preferred embodiment, the disc is a double convex main body where the two convex surfaces are joined by a generally vertically oriented wall member. The wall member may have concave, convex or straight sides. The plane defined by the junction of the upper or superior convex surface and the wall is non-parallel to the plane defined by the junction of the lower or inferior convex surface and the wall, such that the two planes meet to form an angle. The upper and lower convex surfaces may contact at a single point or not at all, in which case the wall member will extend completely around the disc but vary in height. The overall appearance of the disc may be characterized as similar to a clamshell. The convex surfaces may be sections of a sphere or of an ellipsoid, and the two convex surfaces may be identical in configuration or different. The wall member may be circular or elliptical.

Alternatively, the disc may be part of an assembly or combination where one or two vertebral attachment members are affixed directly to one or both adjoining vertebrae in known manner, where the endplates of the vertebrae are damaged or diseased such that they no longer provide the optimum concave surface required to receive and retain the disc without fixation. The assembly may take the form of two vertebral attachment members each having a concave receiving surface which corresponds to the convex surface of the disc. The two vertebral attachment members have base plate members which are permanently affixed to adjoining vertebrae with the disc member retained in between. If only one vertebra is damaged, the assembly may consist of a disk in conjunction with a single vertebral attachment joined to one vertebrae, the vertebral attachment member having a concave surface to receive the disc. The assembly may also consist of a base plate member connected to a disc with a concave surface and a separate vertebral attachment member with a convex surface. In all cases the convex surface is shaped as described above, where the maximum thickness or height is off-center.

DETAILED DESCRIPTION OF THE INVENTION

With reference to the drawings, the invention will now be described in detail with regard for the best mode and preferred embodiments. References to vertical, horizontal, superior, inferior, upper and lower shall be defined in relation to a vertically oriented spine having an anterior-posterior axis and a medial-lateral axis.

Figure 1:
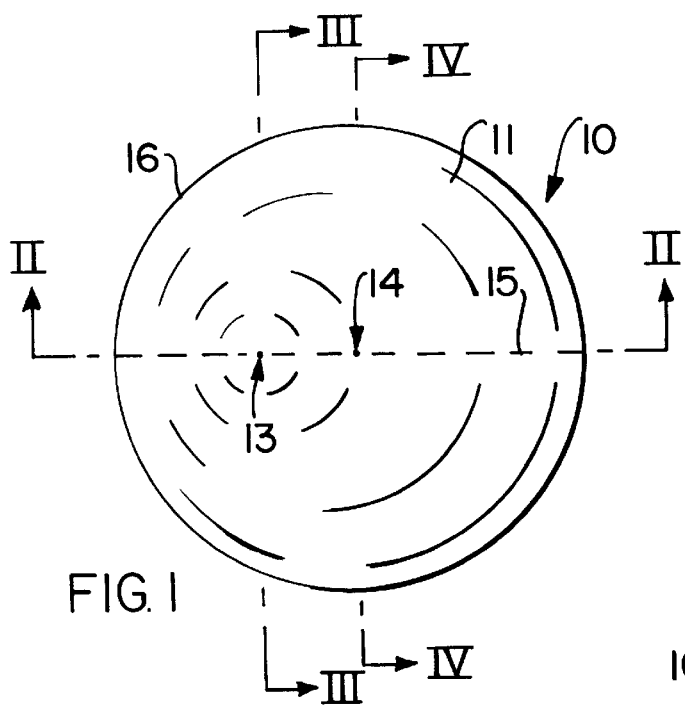
FIG. 1 is a superior view of disc of the invention, showing the main body having a circular periphery.

As shown in FIG. 1, the intervertebral prosthetic disc 10 is a main body having opposing convex surfaces, a superior or upper surface 11 and an inferior or lower surface 12. The disc 10 is composed of a substantially rigid and durable bio-compatible material. The surface may be smooth or provided with undulations or texture. The disc 10 may be formed of plastic, ceramics or metal, or even hydrogel material if enough rigidity is provided. The superior and inferior surfaces 11 and 12 are the contact surfaces which abut a pair of vertebrae, preferably with the disc 10 being inserted directly between the adjoining vertebrae. The double convex configuration of the disc 10 conforms to the general concave shape of the opposing end plate of each vertebra, such that the disc 10 is maintained in proper position by the conjunction of the two opposing concave structures, in combination with pressure from body weight and ligamentotaxis. As shown in FIGS. 1 through 9, the opposing convex surfaces 11 and 12 are joined directly to each other in this embodiment, the juncture shown as forming a circular periphery 16 in FIG. 1 or preferably an elliptical or ovoid periphery in FIG. 5. The periphery 16 may also have other shapes as well to better conform to the patient anatomy in a particular application.

Figure 2:
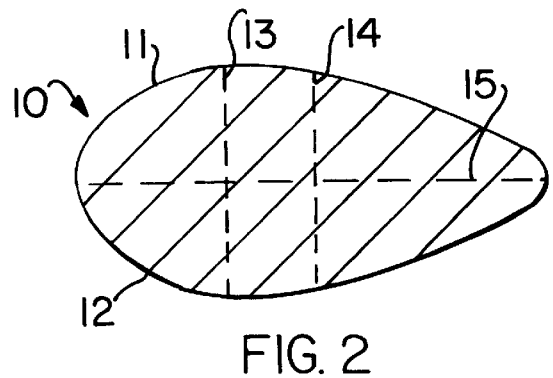
FIG. 2 is a cross-sectional view taken along line II—II of FIG. 1, corresponding to a vertical plane containing the anterior-posterior axis.

In the case of a circular periphery 16, central vertical axis 14 occupies the midpoint of the disc 10. In the case of an elliptical or other non-circular periphery 16, the disc 10 will have a central vertical axis 14 defined as the vertical line passing through the midpoint of the anterior-posterior axis 15, the anterior-posterior axis 15 being parallel to the anterior-posterior of the spine when the disc 10 is inserted and located vertically within the disc 10 at the point of greatest dimension in the anterior-posterior direction. The convex surfaces 11 and 12 have a single point of maximum vertical distance which is not located on the central vertical axis 14, that is, the thickest portion of the disc 10 in the vertical direction is not at the central vertical axis 14. The vertical line passing through this point is defined as the non-central major vertical axis 13. The anterior-posterior axis 15 passes through the non-central major vertical axis 13 and the central vertical axis 14. This design results in an egg-shaped or ovoid cross-sectional configuration along the vertical plane containing the anterior-posterior axis 15, as shown in FIG. 2.

Figure 3:
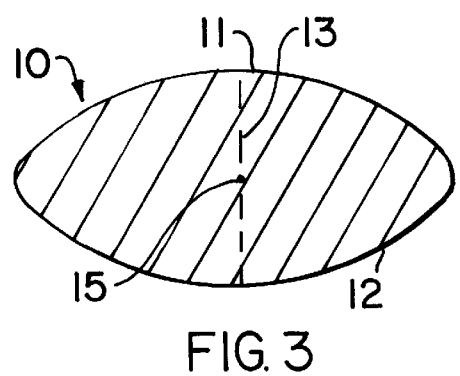
FIG. 3 is a cross-sectional view taken along line III—III of FIG. 1, corresponding to a vertical plane perpendicular to the vertical plane containing the anterior-posterior axis, this plane containing the non-central vertical axis.
Figure 4:
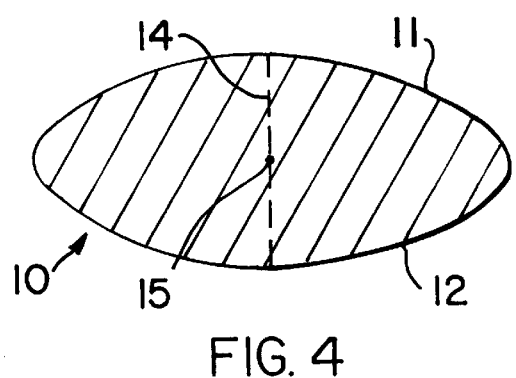
FIG. 4 is a cross-sectional view taken along line IV—IV of FIG. 1, corresponding to a vertical plane perpendicular to the vertical plane containing the anterior-posterior axis, this plane containing the central vertical axis.

Cross-sectional views in the medial-lateral direction are shown in FIGS. 3 and 4. FIG. 3 is a vertical cross-section, perpendicular to the anterior-posterior axis 15, through the thickest portion of the disc 10 and containing the non-central major vertical axis 13. FIG. 4 is a vertical cross-section parallel to the plane of FIG. 3 and containing the central vertical axis 14. The disc 10 is widest at the point along the anterior-posterior axis 15 shown in FIG. 4, but the disc 10 is thickest at the point shown in FIG. 3. The superior convex surface 11 and the inferior convex surface 12 should match the anatomy of the particular patient and may be bilaterally symmetrical along the vertical plane containing the anterior-posterior axis 15. The superior and inferior convex surfaces 11 and 12 may also be symmetrical to each other about the horizontal plane containing the anterior-posterior axis 15. The convex surfaces 11 and 12 may be spherical or elliptical in the lateral-lateral direction.

Figure 10:
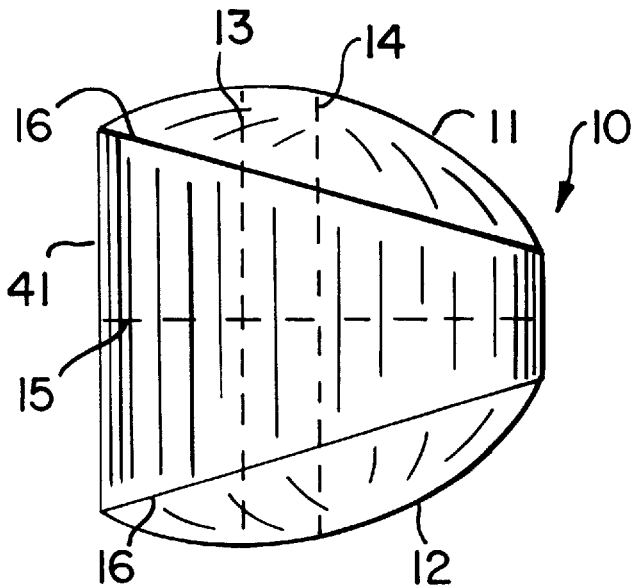
FIG. 10 is a side view of an alternative embodiment of the invention, where the two convex surfaces are sections of a sphere and are connected by a generally vertical wall member.
Figure 11:
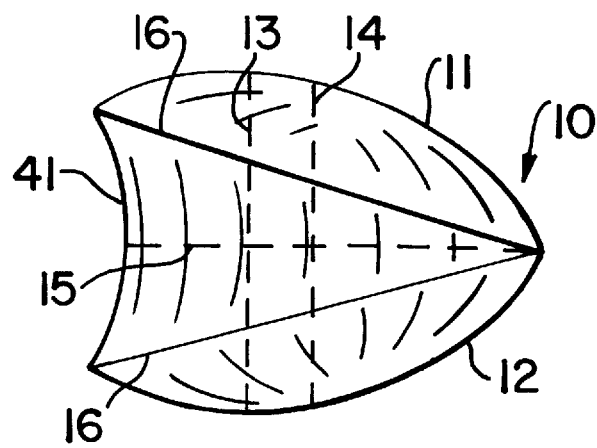
FIG. 11 is a side view of an alternative embodiment of the invention, where the two convex surfaces meet at a point and where the wall member has a concave surface.
Figure 12:
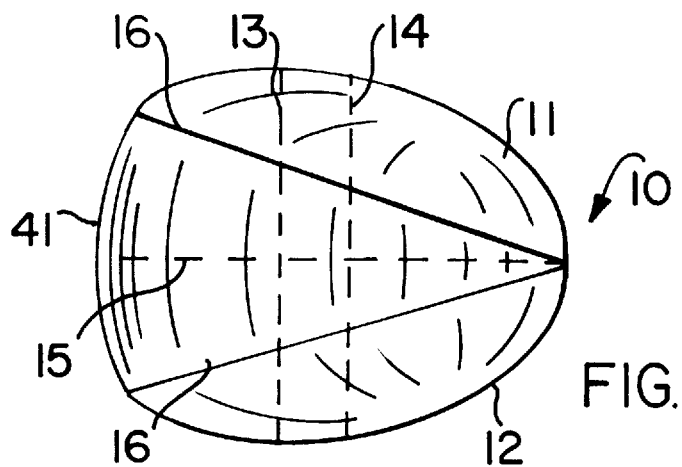
FIG. 12 is a side view of an alternative embodiment of the invention, where the convex surfaces are sections of an ellipsoid and the wall member has a convex surface.

A more preferred embodiment of the device is illustrated in FIGS. 10 though 12. In this embodiment, the disc 10 is comprised of a superior convex surface 11 and an inferior convex surface 12 joined by a generally vertically disposed wall member 41 which extends circumferentially around the disc 10. The periphery junction 16 of the superior convex surface 11 and the upper edge of the wall member 41 defines a first plane, and the periphery junction 16 of the inferior convex surface 12 and the bottom edge of the wall member 41 defines a second plane. The first plane and the second plane so defined are non-parallel, such that they meet at a point to form an angle. This meeting point may be external to the disc 10, as shown in FIG. 10, or the superior convex surface 11 may contact the inferior convex surface 12 at a point, as shown in FIGS. 11 and 12.

The particular dimensions and configuration of the individual elements will vary depending on patient anatomy. The superior and inferior convex surfaces 11 and 12 may be sections of sphere, as seen in FIGS. 10 and 11, or sections of an ellipsoid, as seen in FIG. 12. The wall member 41 may have a straight surface, as seen in FIG. 10, a concave surface, as seen in FIG. 11, or a convex surface, as seen in FIG. 12. The angle of the first and second planes passing through the peripheries 16 may vary. The wall member 41 may be circular or elliptical in horizontal cross-section. Superior convex surface 11 may be identical to or different in configuration from inferior convex surface 12.

By providing a disc 10 where the greatest vertical thickness is off-center, the disc 10 better conforms to the natural concave surfaces of adjoining vertebrae to properly align and separate the vertebrae. Optimum rotational and sliding moments and translations are provided, and the vertebrae retain the disc 10 in proper position without requirement of fixation.

Figure 6:
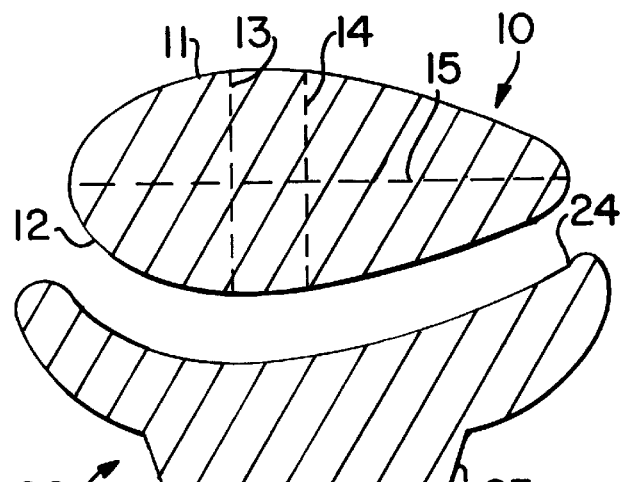
FIG. 6 is a cross-sectional view of an alternative embodiment of the invention, where the disc is retained on one side within the concave surface of a vertebral attachment member.
Figure 5:
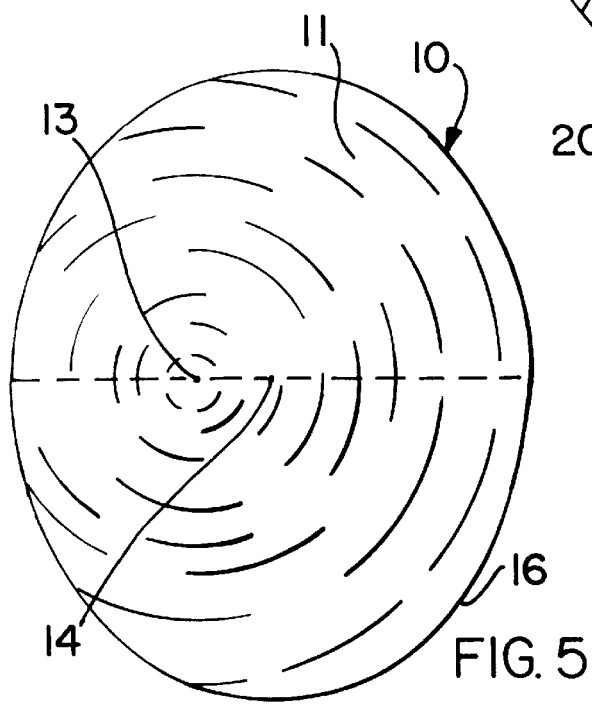
FIG. 5 is a superior view of an alternative embodiment of the invention, showing the disc having an elliptical periphery.

In circumstances where the one or both of the endplates of adjoining vertebrae is not suitable to receive and retain the disc 10 as described above, such as in the case of severe injury or degeneration, the disc 10 is provided with one or two vertebral attachment members 20 which are adapted to be directly affixed to the adjoining vertebra in any commonly known manner. The vertebral endplate is prepared to create a proper receiving surface on the vertebra, and the vertebral attachment member 20 is secured to the vertebra by any of the known methods, such as by cement, e.g., PMMA, bone ingrowth or mechanical means. The vertebral attachment member 20 may be provided with a textured surface or other apertured components to allow natural bone ingrowth to further secure it in place.

Where only one vertebra requires repair, a double convex disc 10 with superior and inferior convex surfaces 11 and 12 as described above, either with or without wall member 41, may be utilized in combination with a separate vertebral attachment member 20, seen in FIG. 6 as comprising a base plate member 23 for direct affixation to the vertebrae, with a concave receiving surface 24 corresponding to either the convex surface 11 or 12, depending on whether the disc 10 is to be superior or inferior to the vertebral attachment member 20. The concave surface 24 of the vertebral attachment member 20 generally mates with or corresponds to the convex surface 11 or 12 to retain the disc 10 while allowing for relative sliding and rotational movement between the two members 10 and 23. The base plate member 23 is fixedly attached to the endplate of a vertebra, while the free surface 11 or 12 of the disc 10 abuts the endplate of the adjacent vertebra.

Figure 7:
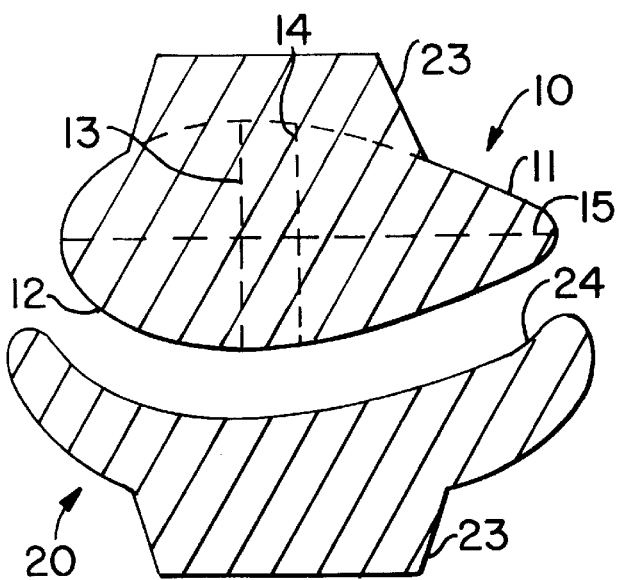
FIG. 7 is a cross-sectional view of an alternative embodiment of the invention, showing a vertebral attachment member having a concave receiving surface and a disc having an attached base plate member.
Figure 8:
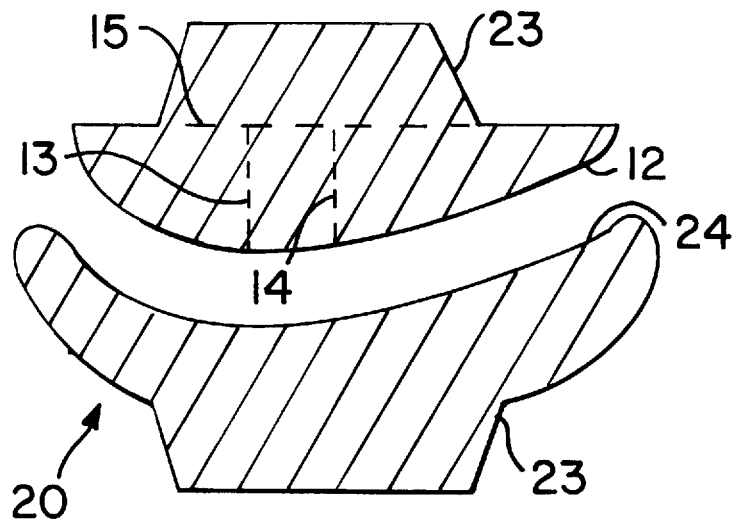
FIG. 8 is a cross-sectional view of an alternative embodiment of the invention similar to FIG. 7, where the disc has only one convex surface.
Figure 9:
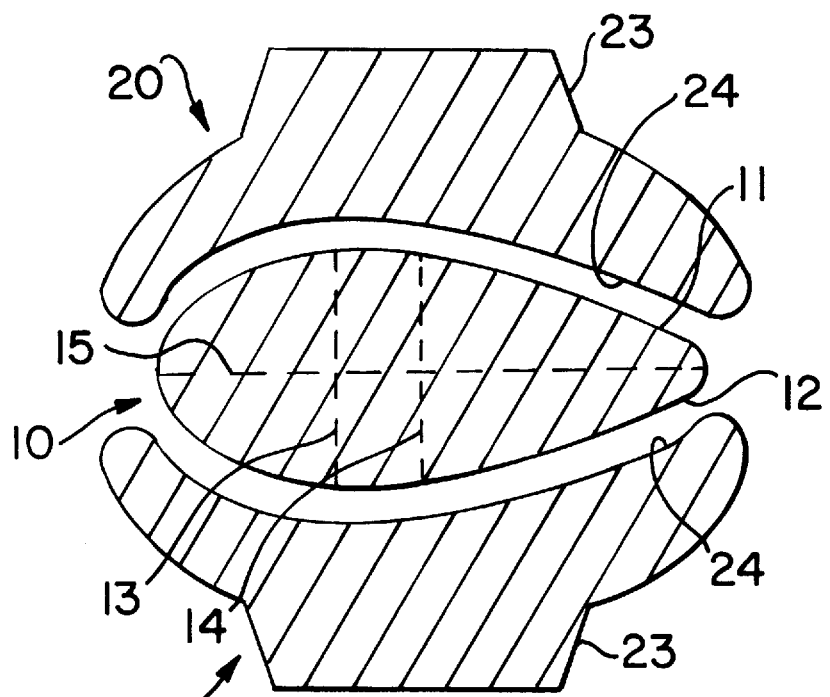
FIG. 9 is a cross-sectional view of an alternative embodiment of the invention, showing the disc retained between the concave surfaces of two vertebral attachment members.

FIGS. 7, 8 and 9 show alternative embodiments for the invention where both endplates of the adjoining vertebrae must be corrected. FIG. 7 shows a combination of an alternatively shaped disc 10 and a vertebral attachment member 20, where the base plate member 23 of the vertebral attachment member 20 is adapted to be secured directly to the prepared vertebra. The concave surface 24 of the vertebral attachment member 20 is shaped to correspond to the convex surface 12 of the disc 10 to generally mate and retain the convex surface 12 to allow for sliding and rotational movement. As shown in FIG. 7, concave surface 24 mates with the inferior convex surface 12 for a situation where the vertebral attachment member 20 is inferior to the disc 10. Alternatively, the members 10 and 20 could be inverted, such that the concave surface 24 would mate with the superior concave surface 11 of disc 10. In this embodiment, a base plate member 23 is attached to the superior surface 11 of disc 10, and this superior base plate member 23 is attached directly to the other vertebral endplate. As before, the disc 10 is configured such that convex surface 12 has a non-central major vertical axis 13 at the most extensive point which is distinct from the central vertical axis 14, both of which pass through the anterior-posterior axis 15.

Alternatively, as seen in FIG. 8, the disc 10 may be configured such that convex surface 12 extends only from the horizontal plane containing the major longitudinal axis 15, with the base plate member 23 extending directly form this horizontal plane. In this embodiment the non-central vertical axis 13 is at the point of greatest dimension between the convex surface 12 and the major longitudinal axis 15, which is distinct from the central vertical axis 14.

Another embodiment of the invention is shown in FIG. 9, where a disc member 10 with opposing convex surfaces 11 and 12 is positioned between both a superior and an inferior vertebral attachment member 20, each of which is adapted to be secured to adjoining vertebrae by base plate members 23. The superior vertebral attachment member 20 has an inferior concave receiving surface 24 which corresponds to the superior convex surface 11 of disc 10, and the inferior vertebral attachment member 20 has a superior concave receiving surface 24 which corresponds to the inferior convex surface 12 of disc 10, such that the disc 10 is received in a manner which allows for relative sliding and rotational movement.

It is understood that equivalents and substitutions to certain elements set forth above may be obvious to those skilled in the art, and the true scope and definition of the invention therefore is to be as set forth in the following claims.

I claim:

1. An intervertebral prosthetic disc composed of a substantially rigid, bio-compatible material, said disc having a pair of opposing convex surfaces, said convex surfaces being an inferior surface and a superior surface, a non-central vertical axis at the point of maximum vertical dimension between said inferior surface and said superior surface, an anterior-posterior axis, a central vertical axis at the midpoint of said anterior-posterior axis, said non-central vertical axis and said vertical axis passing through said anterior-posterior axis, where said superior convex surface is joined to said inferior convex surface by a generally vertically disposed non-linear wall member, where the junction between said wall member and said superior convex surface defines a first plane and where the junction between said wall member and said inferior convex surface defines a second plane, and where said first plane and said second plane are non-parallel.

2. The disc of claim 1, where said convex surfaces are non-spherical in the vertical plane containing said anterior-posterior axis.

3. The disc of claim 1, where said inferior convex surface is bilaterally symmetrical.

4. The disc of claim 1, where said superior convex surface is bilaterally symmetrical.

5. The disc of claim 1, where said main body is circular in a horizontal plane containing said anterior-posterior axis.

6. The disc of claim 1, where said main body is elliptical in a horizontal plane containing said anterior-posterior axis.

7. The disc of claim 1 in combination with a separate vertebral attachment member adapted to be secured to a first vertebra, said vertebral attachment member having a concave surface corresponding to one of said pair of convex surfaces, such that said vertebral attachment member retains said disc in a manner which allows relative sliding and rotational movement.

8. The combination of claim 7, where said convex surface are non-spherical in the vertical plane containing said anterior-posterior axis.

9. The combination of claim 7, where said convex surface are bilaterally symmetrical.

10. The combination of claim 7, where said main body is circular in a horizontal plane containing said anterior-posterior axis.

11. The combination of claim 7, where said main body is elliptical in a horizontal plane containing said anterior-posterior axis.

12. The combination of claim 7, further comprising a second vertebral attachment member adapted to be secured to a second vertebra, said second vertebral attachment member having a concave surface corresponding to the other of said pair of convex surfaces, such that said vertebral attachment members retain said disc in a manner which allows relative sliding and rotational, movement.

13. The combination of claim 12, where said convex surface are non-spherical in the vertical plane containing said anterior-posterior axis.

14. The combination of claim 12, where said convex surface are bilaterally symmetrical.

15. The combination of claim 12, where said main body is circular in a horizontal plane containing said anterior-posterior axis.

16. The combination of claim 12, where said main body is elliptical in a horizontal plane containing said anterior-posterior axis.

17. The disc of claim 1, where said wall member has a convex surface.

18. The disc of claim 1, where said wall member has a concave surface.

19. An intervertebral prosthetic disc assembly comprised of substantially rigid, bio-compatible material, said assembly comprising in combination a disc and a separate vertebral attachment member, said disc comprising a base plate member adapted to be secured to a first vertebra and a convex surface having a non-central maximum vertical dimension, a non-central vertical axis along the line of maximum vertical dimension, an anterior-posterior axis passing through said non-central vertical axis, and where said convex surface is non-spherical in a vertical plane containing said anterior-posterior axis;

said vertebral attachment member comprising a base plate member adapted to be secured to a second vertebra and a concave surface corresponding to said convex surface, such that said concave surface generally mates with said convex surface therein to allow for relative sliding or rotational movement therebetween.

20. The assembly of claim 19, where said convex surface is non-spherical in the vertical plane containing said anterior-posterior axis.

21. The assembly of claim 19, where said convex surface is bilaterally symmetrical.

22. An intervertebral prosthetic disc composed of a substantially rigid, bio-compatible material, said disc having a pair of opposing convex surfaces, said convex surfaces being an inferior surface and a superior surface, a non-central vertical axis at the point of maximum vertical dimension between said inferior surface and said superior surface, an anterior-posterior axis, a central vertical axis at the midpoint of said anterior-posterior axis, said non-central vertical axis and said vertical axis passing through said anterior-posterior axis, where said superior convex surface is joined to said inferior convex surface by a generally vertically disposed wall member, where the junction between said wall member and said superior convex surface defines a first plane and where the junction between said wall member and said inferior convex surface defines a second plane, and where said first plane and said second plane are non-parallel and where said superior convex surface contacts said inferior convex surface.

23. The disc of claim 22, where said wall member has a straight surface.

24. The disc of claim 22, where said wall member has a convex surface.

25. The disc of claim 22, where said wall member has a concave surface.

26. The disc of claim 22, where said convex surfaces are non-spherical in the vertical plane containing said anterior-posterior axis.

27. The disc of claim 22, where said inferior convex surface is bilaterally symmetrical.

28. The disc of claim 22, where said superior convex surface is bilaterally symmetrical.

29. The disc of claim 22, where said main body is circular in a horizontal plane containing said anterior-posterior axis.

30. The disc of claim 22, where said main body is elliptical in a horizontal plane containing said anterior-posterior axis.

31. The disc of claim 22 in combination with a separate vertebral attachment member adapted to be secured to a first vertebra, said vertebral attachment member having a concave surface corresponding to one of said pair of convex surfaces, such that said vertebral attachment member retains said disc in a manner which allows relative sliding and rotational movement.

32. The combination of claim 31, where said convex surfaces are non-spherical in the vertical plane containing said anterior-posterior axis.

33. The combination of claim 31, where said convex surfaces are bilaterally symmetrical.

34. The combination of claim 31, where said main body is circular in a horizontal plane containing said anterior-posterior axis.

35. The combination of claim 31, where said main body is elliptical in a horizontal plane containing said anterior-posterior axis.

36. The combination of claim 31, further comprising a second vertebral attachment member adapted to be secured to a second vertebra, said second vertebral attachment member having a concave surface corresponding to the other of said pair of convex surfaces, such that said vertebral attachment members retain said disc in a manner which allows relative sliding and rotational movement.

37. The combination of claim 36, where said convex surfaces are non-spherical in the vertical plane containing said anterior-posterior axis.

38. The combination of claim 36, where said convex surfaces are bilaterally symmetrical.

39. The combination of claim 36, where said main body is circular in a horizontal plane containing said anterior-posterior axis.

40. The combination of claim 36, where said main body is elliptical in a horizontal plane containing said anterior-posterior axis.

41. An intervertebral prosthetic disc composed of a substantially rigid, bio-compatible material, said disc having a pair of opposing convex surfaces, said convex surfaces being an inferior surface and a superior surface, a non-central vertical axis at the point of maximum vertical dimension between said inferior surface and said superior surface, an anterior-posterior axis, a central vertical axis at the midpoint of said anterior-posterior axis, said non-central vertical axis and said vertical axis passing through said anterior-posterior axis, where said superior convex surface is joined to said inferior convex surface by a generally vertically disposed wall member, where the junction between said wall member and said superior convex surface defines a first plane and where the junction between said wall member and said inferior convex surface defines a second plane, and where said first plane and said second plane are non-parallel and where said superior convex surface and said inferior convex surface are each sections of a sphere.

42. The disc of claim 41, where said wall member has a straight surface.

43. The disc of claim 41, where said wall member has a convex surface.

44. The disc of claim 41, where said wall member has a concave surface.

45. The disc of claim 41, where said main body is circular in a horizontal plane containing said anterior-posterior axis.

46. The disc of claim 41, where said main body is elliptical in a horizontal plane containing said anterior-posterior axis.

47. The disc of claim 41 in combination with a separate vertebral attachment member adapted to be secured to a first vertebra, said vertebral attachment member having a concave surface corresponding to one of said pair of convex surfaces, such that said vertebral attachment member retains said disc in a manner which allows relative sliding and rotational movement.

48. The combination of claim 47, where said main body is circular in a horizontal plane containing said anterior-posterior axis.

49. The combination of claim 47, where said main body is elliptical in a horizontal plane containing said anterior-posterior axis.

50. The combination of claim 47, further comprising a second vertebral attachment member adapted to be secured to a second vertebra, said second vertebral attachment member having a concave surface corresponding to the other of said pair of convex surfaces, such that said vertebral attachment members retain said disc in a manner which allows relative sliding and rotational movement.

51. The combination of claim 50, where said main body is circular in a horizontal plane containing said anterior-posterior axis.

52. The combination of claim 50, where said main body is elliptical in a horizontal plane containing said anterior-posterior axis.

53. An intervertebral prosthetic disc for placement between two adjacent vertebrae, said disc consisting of a substantially rigid, non-porous, bio-compatible material, said disc having a pair of opposing convex surfaces, said convex surfaces being an inferior surface and a superior surface, a non-central vertical axis at the point of maximum vertical dimension between said inferior surface and said superior surface, an anterior-posterior axis, a central vertical axis at the midpoint of said anterior-posterior axis, said non-central vertical axis and said vertical axis passing through said anterior-posterior axis, where said convex surfaces are not fixed to said adjacent vertebrae such that said disc has free movement relative to said adjacent vertebrae.

54. The disc of claim 53, where said convex surfaces are non-spherical in the vertical plane containing said anterior-posterior axis.

55. The disc of claim 53, where said inferior convex surface is bilaterally symmetrical.

56. The disc of claim 53, where said superior convex surface is bilaterally symmetrical.

57. The disc of claim 53, where said main body is circular in a horizontal plane containing said anterior-posterior axis.

58. The disc of claim 53, where said main body is elliptical in a horizontal plane containing said anterior-posterior axis.

\* \* \* \* \*